US00PP10693P

United States Patent [19]

Mak

[11] Patent Number: Plant 10,693

[45] Date of Patent: Nov. 17, 1998

[54] ASIATIC HYBRID LILY PLANT NAMED 'EUROGOLD'

[76] Inventor: Johan A. Mak, 5955 Halls Ferry Rd., Independence, Oreg. 97351

[21] Appl. No.: 918,651

[22] Filed: Aug. 22, 1997

[51] Int. Cl.[6] ..... A01H 5/00

[52] U.S. Cl. ..... Plt./87.4

[58] Field of Search ..... Plt./87.4

[56] References Cited

U.S. PATENT DOCUMENTS

| | | | |
|---|---|---|---|
| P.P. 5,008 | 3/1983 | McRae | Plt./87.4 |
| P.P. 5,979 | 5/1987 | McRae | Plt./87.4 |
| P.P. 6,422 | 11/1988 | McRae | Plt./87.4 |
| P.P. 8,365 | 9/1993 | Vletter | Plt./87.4 |

*Primary Examiner*—Howard J. Locker

[57] ABSTRACT

A new variety of a hybrid lily plant bearing semi-upright flowers of excellent form and long persistence, both on the plant and as cut-flowers. The flowers of the new plant are particularly characterized by buds which show their actual color, and their spotless deep yellow coloration all over the flower surrounding a small dark brown ray extending from the nectary furrows. This combination is completely new in the Asiatic hybrid divisions of lilies suited to forcing and to mass commercial cultivation. The variety is highly resistant to botrytis disease and shows high tolerance to virus. The bulbs may be precooled and forced for cut-flower production. The clone is vigorous and is a good grower and propagator.

1 Drawing Sheet

BACKGROUND OF THE INVENTION

My new variety of lily plant originated as a seedling which first flowered in 't Zand, Netherlands, in 1989. The breeding efforts had as their objective the production of large-flowered Asiatic hybrids in spotless yellow coloration, flowers in upright position, and a tall stem suited to forcing into flower out of season, heretofore unknown in the lily breeding art.

I achieved the desired objective by intercrossing selected almost clean yellow Asiatic seedlings with tall stems suited to forcing for year-round use as cut-flowers and carrying the recessive gene for spotless yellow.

The flowers of my new lily are characterized by large size and broad-tepalled "bowl-shaped" form, unusually thick substance, and deep and intense coloration without any tepal spotting which surrounds a small dark brown ray extending from the nectary furrows. When the flower ages a small orange flame will be visible close to the center of its tepals. It possesses unusually strong, tall stems. In addition, the clone possesses to a high degree desirable characteristics of hybrid vigor. The clone is a good grower and propagator, as observed at 't Zand, Netherlands, and at Salem, Oreg.

My new variety of lily plant has been asexually reproduced by me and under my direction a 't Zand, Netherlands, and at Salem, Oreg. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing, which shows the open bloom in full color and illustrates the flower form, the tepal arrangement and in particular the novel and distinctive flower coloration with its intense spotless yellow coloration surrounding a small dark brown ray extending from the nectary furrows and its flowers in upright position.

DESCRIPTION OF THE NEW VARIETY

The following is a detailed description of my new variety of Oriental hybrid lily, with nomenclature according to the *International Lily Register* (The Royal Horticultural Society of London, Second Edition, 1969), and with color designations according to the Color Chart of The Royal Horticultural Society, published by the Society in 1966.

The Plant

Origin: Seedling.

*Seed parent*.—Selected unnamed yellow Seedling.

*Pollen parent*.—Selected unnamed yellow Seedling.

Commercial classification: Hybrid Lilium clone.

Horticultural classification: Division 1-A, upright Asiatic hybrid lily, according to the Horticultural Classificatiion of Lilies, Royal Horticultural Society of London.

Form: Single stem, erect and stately,

Height: 100 to 150 cm from bulbs 14 to 18 cm in circumference, provided light levels are adequate, low light levels may cause "stretching."

Growth: Vigorous and upright.

Foliage quantity: Abundant.

Shape of leaf: Lanceolate (pointed).

Texture: Leathery and glossy.

Color: Green R.H.S. CC 137A, lighter on lower side.

Bulb:

*Size*.—Any size, ranging to 25 cm circumference commercially

*Color*.—White, with flushes of pink and yellow after exposure to light.

Form: Obtuse, ovoid, and long.

Size: 8 to 11 cm long and 7 to 9 cm in circumference just prior to opening

Color of end of bud: Greenish.

Color of midrib: Close to R.H.S. CC 139D.

Opening: Bud opens slowly, in response to morning light; this takes about one hour.

Color: Close to R.H.S. CC 13C.

Peduncle: Averages 9 to 13 cm, but it may elongate if light levels are too low or if bulbs have been improved stored to prior forcing. Color is close to R.H.S. CC 141C.

The Flower

Blooming habit: Annually in midseason; flowers once and profusely.
Size: Flowers are medium large-sized, averaging 15 to 19 cm in diameter, the outer tepals are 2.5 to 3.50 cm wide, and the inner tepals are 4 to 5.5 cm wide.
Borne: In a single racemic inflorescence producing 9 to 13 flowers from a bulb 14 to 16 cm in circumference.
Shape: Form a somewhat bowl shape by the second day after opening.
Tepalage: Typical of genus Lilium, with 6 imbricated tepals.
Tepal:
*Color*.—R.H.S. CC Yellow Group 12A. Inner base of tepal: R.H.S. CC Yellow Group 12A. Tepal spotting: None.
*Longevity*.—Tepals stay on stems about three weeks.
*Pedicel Length*.—Average 7 to 12 cm long.
*Color*.—Dark green with dark plum overlay.
*Form*.—Sturdy and ascending.
Appearance: Flower is shiny.
Disease resistance: The flower and plant are resistant to disease: in particular, they are resistant to viruses and Botrytis blight.
Fragrance: None.
Lasting quality: The flower is long lasting, both on the plant and as a cut-flower.

The Reproductive Organs

Stamens: Arrangement typical of genus Lilium. Six stamens with soft green to palest pink filaments 5 to 7 cm long.
Pollen and anthers (dehisced): R.H.S. CC Orange Group 24A.
Pistil: One in number, 7 to 9 cm long.
Stigma: R.H.S. CC 60D.
Chracteristics of ovary: Characteristic of genus Lilium.

The Fruit

Fertility: The fruit bears fertile seed.
Shape: Ovoid.
Color at maturity: Soft brown, sometimes overlaid with soft plum.

'Eurogold' most nearly resembles 'Polyanna' (U.S. Plant Pat. No. 5,979), but differs from same in flower shape, coloration, and in the lack of tepal shooting (pappillae).

I claim:

1. A new and distinctive variety of Asiatic hybrid lily plant substantially as herein shown and described, characterized by its high resistance to disease; its tolerance of virus and botrytis blight, its vigorous growth and rapid natural propagation; the excellence of its flower form, size, and substance; its versatility both as a garden plant and as a cut-flower producer from pre-cooled bulbs forced under glass out of season; and in particular by its unique semi upright-facing spotless flowers with its clean and intense yellow coloration surrounding a small dark brown ray extending from the nectary furrows and its small orange flame when the flower ages, a combination unique among Asiatic hybrid lilies suited to forcing and to mass commercial cultivation.

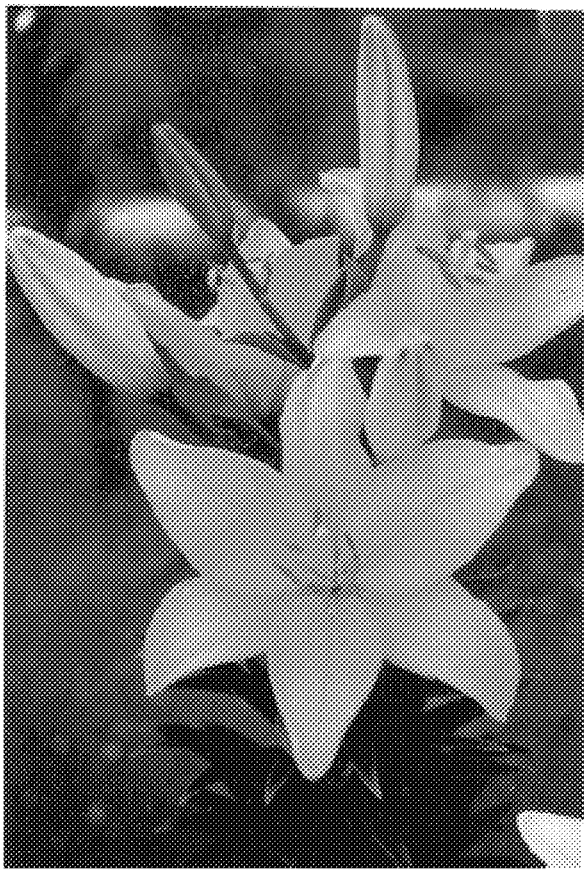

* * * * *